(12) United States Patent
Schnorr et al.

(10) Patent No.: US 11,608,377 B2
(45) Date of Patent: Mar. 21, 2023

(54) ENHANCED DEPLETION OF TARGETED CELLS WITH CD47 BLOCKADE AND AN IMMUNE COSTIMULATORY AGONIST

(71) Applicant: The Board of Trustees of the Leland Stanford Junior University, Stanford, CA (US)

(72) Inventors: Peter J. Schnorr, Sudbury, MA (US); Akanksha Chhabra, San Francisco, CA (US); Judith A. Shizuru, Palo Alto, CA (US); Irving L. Weissman, Stanford, CA (US); Kipp Andrew Weiskopf, Brookline, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/119,548

(22) Filed: Dec. 11, 2020

(65) Prior Publication Data
US 2021/0095034 A1    Apr. 1, 2021

Related U.S. Application Data

(63) Continuation of application No. 15/754,757, filed as application No. PCT/US2016/049016 on Aug. 26, 2016, now Pat. No. 10,894,831.

(60) Provisional application No. 62/210,279, filed on Aug. 26, 2015.

(51) Int. Cl.
| | | |
|---|---|---|
| C07K 16/28 | (2006.01) | |
| C07K 16/30 | (2006.01) | |
| C07K 14/525 | (2006.01) | |

(52) U.S. Cl.
CPC ........ *C07K 16/2818* (2013.01); *C07K 14/525* (2013.01); *C07K 16/2848* (2013.01); *C07K 16/2878* (2013.01); *C07K 16/2896* (2013.01); *C07K 16/30* (2013.01); *C07K 2319/00* (2013.01)

(58) Field of Classification Search
CPC .......... C07K 14/70596; C07K 16/2818; C07K 14/525; C07K 16/2896; C07K 2317/75; C07K 2317/76; C07K 16/30; C07K 16/2878; C07K 16/2848; C07K 16/2803; A61P 35/00; A61P 37/02; A61K 35/17; A61K 38/1709; A61K 2039/507; A61K 2039/57; A61K 51/00; A61K 2123/00; A61K 2121/00; A61K 2800/00; A61K 2039/555; A61K 2039/505; A61K 39/00; A61K 33/00
See application file for complete search history.

(56) References Cited

U.S. PATENT DOCUMENTS

| | | |
|---|---|---|
| 2011/0177104 A1 | 7/2011 | Kwon et al. |
| 2012/0282174 A1 | 11/2012 | Weissman et al. |
| 2013/0011401 A1 | 1/2013 | Huber et al. |
| 2014/0363442 A1 | 12/2014 | Frazier et al. |

FOREIGN PATENT DOCUMENTS

| | | |
|---|---|---|
| JP | 2018525421 | 9/2018 |
| WO | WO2004/002425 | 1/2004 |
| WO | WO 2011/034969 | 3/2011 |
| WO | WO 2013/109752 | 7/2013 |
| WO | WO2015069703 | 5/2015 |
| WO | WO 2015/191861 | 6/2015 |
| WO | WO2015105995 | 7/2015 |
| WO | WO 2016/023040 | 2/2016 |
| WO | WO2016/033201 | 3/2016 |
| WO | WO 2016/063233 | 4/2016 |
| WO | WO 2017/027422 | 2/2017 |
| WO | WO2017035480 | 2/2017 |

OTHER PUBLICATIONS

Hatherley et al., "The structure of the macrophage signal regulatory protein alpha (SIRPalpha) inhibitory receptor reveals a binding face reminiscent of that used by T cell receptors", J Biol Chem., May 11, 2007, pp. 14567-14575, vol. 282, No. 19, The American Society for Biochemistry and Molecular Biology, Inc., Rockville, MD.

Ho et al., ""Velcro" Engineering of High Affinity CD47 Ectodomain as Signal Regulatory Protein a (SIRPa) Antagonists That Enhance Antibody-dependent Cellular Phagocytosis", The Journal of Biological Chemistry, Apr. 2, 2015, pp. 12650-12663, vol. 290, No. 20, The American Society for Biochemistry and Molecular Biology, Inc., Rockville, MD.

Kim et al., "Stimulation with 4-1BB (CD137) inhibits chronic graft-versus-host disease by inducing activation-induced cell death of donor CD4 + T cells", Blood, Nov. 2, 2004, pp. 2206-2213, vol. 105, No. 5, The American Society of Hematology, Washington, D.C.

Kohrt et al., "Combination strategies to enhance antitumor ADCC", Immunotherapy, May 2012, pp. 511-527, 4(5), Future Medicine Ltd., London, United Kingdom.

(Continued)

*Primary Examiner* — Bao Q Li
(74) *Attorney, Agent, or Firm* — Pamela J. Sherwood; Bozicevic, Field & Francis LLP

(57) ABSTRACT

Methods are provided for targeting cells for depletion, including without limitation tumor cells, in a regimen comprising contacting the targeted cells with a combination of agents that modulate immunoregulatory signaling. Immunoregulatory modulating agents include (i) an agent that blockades CD47 activity; and (ii) an agent that agonizes an immune costimulatory molecule, e.g. CD137. The regimen may further comprise an agent that specifically binds to the target cell, e.g. an antibody or biologically active fragment or derivative thereof. The level of depletion of the targeted cell is enhanced relative to a regimen in which a single immunoregulatory modulating agent is used; and the effect may be synergistic relative to a regimen in which a single immunoregulatory modulating agent is used.

15 Claims, 1 Drawing Sheet

(56) References Cited

OTHER PUBLICATIONS

Lee et al., "Novel structural determinants on SIRPα that mediate binding to CD47", J. Immunol., Dec. 1, 2007, pp. 7741-7750, vol. 179, Issue 11, The American Association of Immunologists, Inc., Rockville, MD.

Lee et al., "The Role of cis Dimerization of Signal Regulatory Protein α (SIRPα) in Binding to CD47", J Biol Chern., Dec. 3, 2010, pp. 37953-37963, 285(49), The American Society for Biochemistry and Molecular Biology, Inc., Rockville, MD.

Weiskopf et al., "Engineered SIRPa Variants as Immunotherapeutic Adjuvants to Anticancer Antibodies", Science, May 30, 2013, p. 88-91, vol. 341, American Association for the Advancement of Science, Washington, DC.

Ishikawa et al., "An assay for long-term engrafting human hemopoietic cells based on newborn NOD/SCID Beta 2-microglobulin(null) mice", Experimental Hematology, Jan. 22, 2002, pp. 488-494, 30(5), Elsevier, Amsterdam, Netherlands.

Chhabra et al., "Hematopoietic stem cell transplantation in immunocompetent hosts without radiation or chemotherapy", Science Translational Medicine, Aug. 10, 2016, pp. 351ra105-351ra105, vol. 8, Issue 351, American Association for the Advancement of Science, Washington, D.C.

Liu et al., "CD47 blockade ,-triggers T cell-mediated destruction of //immunogenic tumors", Nature Medicine, Oct. 31, 2015, pp. 1289-1215, vol. 21, No. 18, Springer Nature, Berlin, Germany.

Lucido et al., "CD137 Enhancement of HPV Positive Head and Neck Squamous Cell Carcinoma Tumor Clearance", Vaccines, Dec. 10, 2014, pp. 841-853, vol. 2, No. 4, MDPI, Basel, Switzerland.

Sockolosky et al., "Durable antitumor responses to CD47 blockade require adaptive immune stimulation", PNAS, May 18, 2016, pp. E2646-E2654, vol. 113, No. 19, National Academy of Sciences, Washington, D.C.

Chester et al., "Dual antibody therapy to harness the innate antitumor immune response to enhance antibody targeting of tumors", Current Opinion in Immunology, 2015, 33:1-8.

Gauttier et al., (2016) "Dual targeting of adaptive and innate immune checkpoints induce potent memory anti-tumor response", European Journal of Cancer, 61(1): S216- S217, Abstract No. 929.

Houot et al., (2011) "Targeting immune effector cells to promote antibody-induced cytotoxicity in cancer immunotherapy" Trends Immunol, 32(11):510-516.

Houot et al., (2012) "Boosting antibody-dependant cellular cytotoxicity against tumor cells with a CD137 stimulatory antibody," Oncoimmunology, 1:6, 957-958.

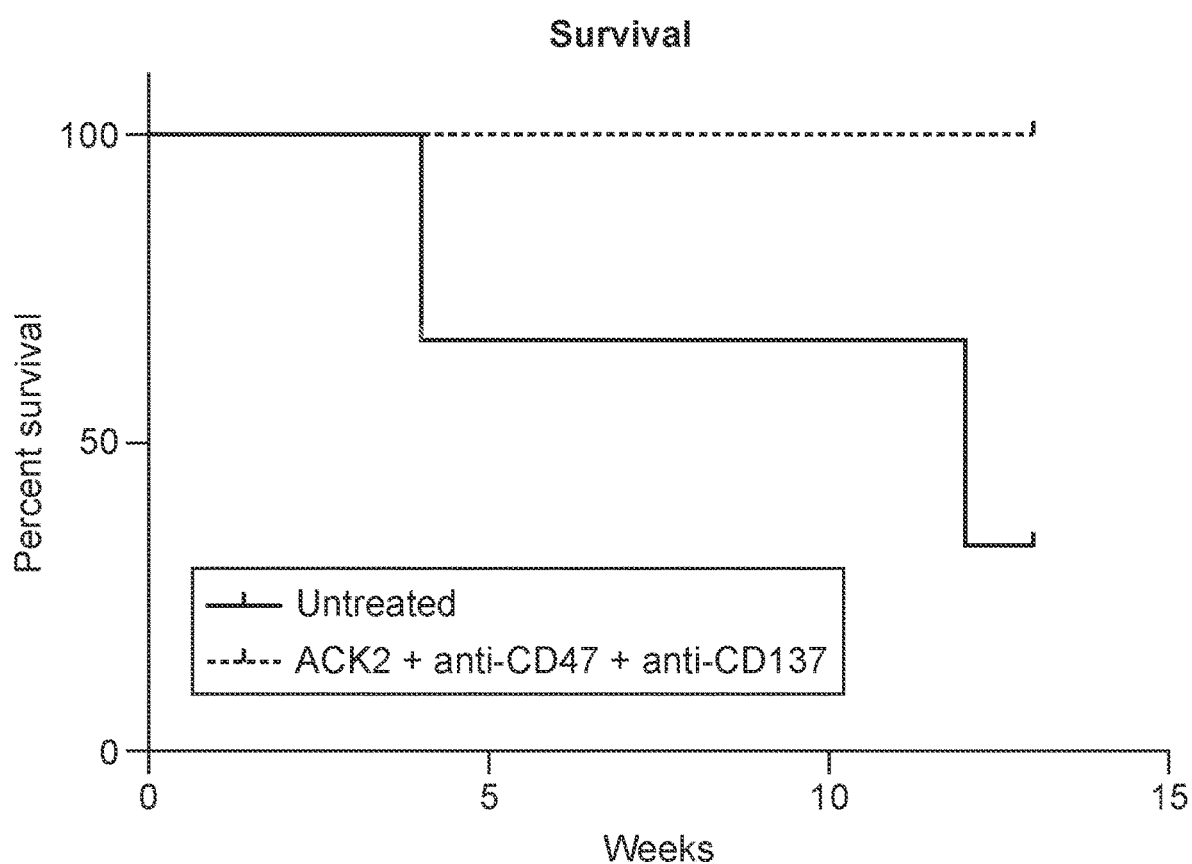

ENHANCED DEPLETION OF TARGETED CELLS WITH CD47 BLOCKADE AND AN IMMUNE COSTIMULATORY AGONIST

CROSS-REFERENCE

This application is a Continuation and claims the benefit of 371 application Ser. No. 15/754,757, filed Feb. 23, 2018, which claims the benefit of PCT Application No. PCT/US2016/049016, filed Aug. 26, 2016, which claims benefit of U.S. Provisional Patent Application Ser. No. 62/210,279 filed Aug. 26, 2015, which applications are incorporated herein by reference in their entirety.

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Discrimination of the healthy from the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells or present in an altered conformation. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Alternatively, blocking SIRPα recognition also allows engulfment of targets that are not normally phagocytosed.

CD47 is a broadly expressed transmembrane glycoprotein with a single Ig-like extracellular domain and five membrane spanning regions. CD47 functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including monocytes and hematopoietic stem cells. Structural determinants on SIRPα that mediate CD47 binding are discussed by Lee et al. (2007) J. Immunol. 179: 7741-7750; Hatherley et al. (2007) J.B.C. 282:14567-75; and the role of SIRPα cis dimerization in CD47 binding is discussed by Lee et al. (2010) J.B.C. 285:37953-63.

Immune cells such as T cells and NK cells are also regulated by signaling pathways, including an antigen nonspecific co-stimulatory signal, which may be provided by molecules on antigen presenting cells that engage particular costimulatory receptors on the immune cells. Costimulation is crucial to the development of an effective immune response of adaptive immunity.

One of the best characterized costimulatory receptors expressed by T cells is CD28, which interacts with CD80 (B7-1) and CD86 (B7-2) on the membrane of APCs. CD28 is constitutively expressed on almost all T cells, and is the major costimulatory receptor for naive T cells. Several members of the tumor necrosis factor receptor (TNFR) family function after initial T cell activation to sustain T cell or NK cell responses. The effects of these costimulatory TNFR family members can often be functionally, temporally, or spatially segregated from those of CD28 and from each other.

TNFR family members can recruit TNF receptor-associated factor (TRAF) adapter proteins and activate the nuclear factor κB (NF-κB) signaling pathway, making them fundamentally distinct from costimulators such as CD28 or ICOS. CD40 and its ligand, CD154, were the first costimulatory molecules to be identified as members of the TNFR/TNF superfamily and are crucial for the functions of B cells and dendritic cells (DCs). Studies of the CD27/CD70, CD30/CD30L, OX40/OX40L, 4-1 BB (CD137)/4-1 BBL, glucocorticoid-induced TNF receptor (GITR)/GITR ligand, herpes virus entry mediator (HVEM)/(LIGHT) pathways indicate that these TNFR/TNF family members provide important costimulatory signals. With the exception of CD27, the TNFR are expressed only upon T-cell or NK cell activation.

Recent work indicates that OX40/OX40L and CD137/CD137L interactions have key roles in regulating the balance between effector and Treg responses. A major role of CD137 is for survival of activated and memory T cells, with preferential effects on $CD8_+$ T cells. However, when other costimulatory signals are limiting, CD137 signals can cooperate with TCR-induced signals to enhance proliferation and development of effector function. Upon Fc receptor triggering, human NK cells upregulate CD137, thereby enhancing the killing function of these activated NK cells. Agonistic anti-CD137 monoclonal antibodies (BMS-663513; Urelumab) are currently in clinical trials as a monotherapy, or combined with tumor specific antibodies for the treatment of cancer.

SUMMARY OF THE INVENTION

Methods are provided for targeting cells for depletion, including without limitation tumor cells, in a regimen comprising contacting the targeted cells with a combination of agents that modulate immunoregulatory signaling. Immunoregulatory modulating agents include (i) an agent that blockades CD47 activity; and (ii) an agent that agonizes an immune costimulatory molecule, e.g. CD137. The regimen may further comprise an agent that specifically binds to the target cell, e.g. an antibody or biologically active fragment or derivative thereof. The level of depletion of the targeted cell is enhanced relative to a regimen in which a single immunoregulatory modulating agent is used; and the effect may be synergistic relative to a regimen in which a single immunoregulatory modulating agent is used.

The agents in the combination are administered concomitantly, i.e. each agent is administered within about 7 days, 6 days, 5 days, 4 days, 3 days, 2 days, 1 day or substantially simultaneously with respect to the other agent(s) in the combination. Administration may be repeated as necessary for depletion of the targeted cell population.

In some embodiments the CD47 blockade is accomplished by administering a soluble SIRPα polypeptide, which may be a high affinity SIRPα variant polypeptide. In other embodiments, antibodies specific for one or both of SIRPα and CD47 are administered. In some embodiments the costimulatory agonist is an antibody that selectively binds to the costimulatory molecule, e.g. an agonist anti-CD137 antibody.

The contacting of a targeted cell may be performed in vivo, e.g. for therapeutic purposes, and in vitro, e.g. for screening assays and the like. In related embodiments, tumor cells, e.g. solid tumors such as carcinomas, sarcomas, melanomas, etc.; leukemias; lymphomas, etc. are targeted for depletion by contacting the immune cells, including phagocytic cells, NK cells, T cells, etc. in proximity of the tumor cells with a combination of a CD47 blocking agent that is effective to block the interaction between CD47 and SIRPα, and an agent that agonizes an immune costimulatory molecule, e.g. CD137. Optionally an agent that specifically binds to the targeted cell is included in the combination. In these aspects, the combination of immunoregulatory agents can be combined with monoclonal antibodies directed against one or more additional tumor cell markers, which compositions can be synergistic in enhancing phagocytosis and elimination of tumor cells as compared to the use of single agents. The effective dose of the combined agents increases the depletion of the tumor cells.

BRIEF DESCRIPTION OF THE FIGURES

FIG. 1. Mastocytoma survival curve.

DETAILED DESCRIPTION OF THE EMBODIMENTS

Methods are provided for the targeted depletion of cells in a subject, where targeted cells are selectively ablated by a combination of agents that modulate immunoregulatory pathways in the subject. One agent that modifies immunoregulatory signaling blocks CD47 signaling. The second agent is an agonist of an immune costimulatory molecule, e.g. CD137.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Anti-CD47 agent. CD47 is a broadly expressed transmembrane glycoprotein with a single Ig-like domain and five membrane spanning regions, which functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα-derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies, for example comprising an IgG4 Fc region, (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the native CD47 sequence.

Immunoregulatory signaling molecules. In addition to the CD47/SIRPα axis, immunoregulatory signaling molecules may include costimulatory polypeptides expressed on immune cells, e.g. T cells, NK cells, antigen presenting cells, etc. Activation, i.e. agonism, of the costimulatory molecule enhances the effector cell function. Many such costimulatory molecules are members of the tumor necrosis factor receptor family (TNFR), e.g. OX40, GITR, CD30, ICOS, etc. TNFR-related molecules do not have any known enzymatic activity and depend on the recruitment of cytoplasmic proteins for the activation of downstream signaling pathways.

A costimulatory molecule of interest is CD137, which may also be referred to as Ly63, ILA or 4-1 BB, and which is a member of the tumor necrosis factor (TNF) receptor family. Members of this receptor family and their structurally related ligands are important regulators of a wide variety of physiologic processes and play an important role in the regulation of immune responses. CD137 is expressed by activated NK cells, T and B lymphocytes and monocytes/macrophages. The gene encodes a 255-amino acid protein with 3 cysteine-rich motifs in the extracellular domain (characteristic of this receptor family), a transmembrane region, and a short N-terminal cytoplasmic portion containing potential phosphorylation sites. Expression in primary cells is strictly activation dependent. The ligand for the receptor is TNFSF9. Human CD137 is reported to bind only to its ligand. Agonists include the native ligand (TNFSF9), aptamers (see McNamara et al. (2008) J. Clin. Invest. 118: 376-386), and antibodies.

Two fully humanized mAbs of CD137, urelumab (BMS-663513) and PF-05082566, have been developed for clinical use. Urelumab is a fully human IgG4 mAb, and PF-05082566 is a fully human IgG2 mAb.

CD134. OX40 (CD134) and its binding partner, OX40L (CD252), are members of the TNFR super-family. OX40 expression is induced following TCR/CD3 cross-linking, and by the presence of inflammatory cytokines, including IL-1, IL-2, and TNF-α. In humans, a substantial proportion of tumor-infiltrating CD4 T cells express OX40. Similarly, activated peripheral CD8 T cells have also been shown to express OX40. Ligation of OX40 on CD8 and conventional (non-regulatory) CD4 T cells, using either its natural ligand (OX40L) or agonist antibodies, promotes their survival and expansion.

Treatment with agonist anti-OX40 monoclonal antibodies (mAbs) along with TCR stimulation in wild-type animals induces expansion, differentiation, and increased survival of CD4 and CD8 T cells. Anti-OX40 administration can overcome CD8 T cell tolerance to a self-antigen and restored their cytotoxic activity, highlighting the therapeutic potential for OX40 agonists. This is of particular importance for patients with cancer, as T cell tolerance to the tumor is a major obstacle for therapeutic modalities.

The use of anti-OX40 monotherapy was tested in a Phase 1 trial in patients with solid tumors. Phase 1 clinical trials investigating OX40 agonists including NCT02318394, NCT02205333, and NCT02221960, with the biological MED16383.

Agonistic OX40 agents can enhance the efficacy of anti-CD47 agents. Agonistic OX40 agents may be administered substantially simultaneously with anti-CD47 agents; or may be administered prior to and concurrently with treatment with anti-CD47 to simulate priming of tumor-specific T cell clones that can be expanded through the OX40 agent.

CD30. The transmembrane receptor CD30 (TNFRSF8) and its ligand CD30L (CD153, TNFSF8) are members of the tumor necrosis factor (TNF) superfamily and display restricted expression in subpopulations of activated immune cells. CD30 is a type I transmembrane glycoprotein of the TNF receptor superfamily. The ligand for CD30 is CD30L (CD153). The binding of CD30 to CD30L mediates pleiotropic effects including cell proliferation, activation, differentiation, and apoptotic cell death. Antibodies in clinical trials for cancer include CD30 agonists SGN-30; XmAb2513 and MDX-1401.

GITR. Glucocorticoid-Induced TNFR-Related (GITR) protein belongs to tumor necrosis factor receptor/tumor necrosis factor superfamily and stimulates both the acquired and innate immunity. It is expressed in several cells and tissues, including T and Natural Killer (NK) cells and is activated by its ligand, GITRL, mainly expressed on antigen presenting cells and endothelial cells. GITR/GITRL system participates in the development of autoimmune/inflammatory responses and potentiates response to infection and tumors by mechanisms including NK-cell co-activation. Antibodies in clinical trials include the GITR agonist TRX518.

Inducible costimulator (ICOS). ICOS is a member of the CD28 family. ICOS expression, may be readily detectable resting, but it upregulated upon activation. ICOS and ICOS-L appear to be a monogamous pair. ICOS costimulation enhances effector functions. ICOS specific agonist antibodies GSK3359609 or JTX-2011 target and bind to ICOS expressed on tumor infiltrating CD4-positive T cells. This stimulates ICOS-positive T-cell proliferation, enhances cytotoxic T-lymphocyte (CTL) survival and increases CTL-mediated immune responses against tumor cells. ICOS, a T-cell specific, CD28-superfamily costimulatory molecule and immune checkpoint protein, is normally expressed on certain activated T cells and plays a key role in the proliferation and activation of T cells.

Agonists includes the native ligands, as described above, aptamers, antibodies specific for an inducible costimulatory molecule that activate the receptor, and derivatives, variants, and biologically active fragments of antibodies that selectively bind to a costimulatory molecule. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein.

Fragments of the ligand or antibodies specific for a costimulatory molecule, particularly biologically active fragments and/or fragments corresponding to functional domains, are of interest. Fragments of interest will typically be at least about 10 aa to at least about 15 aa in length, usually at least about 50 aa in length, but will usually not exceed about 200 aa in length, where the fragment will have a contiguous stretch of amino acids that is identical to the polypeptide from which it is derived. A fragment "at least 20 aa in length," for example, is intended to include 20 or more contiguous amino acids from, for example, an antibody specific for CD137, or from TNFSF9. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods. A "fusion" polypeptide is a polypeptide comprising a polypeptide or portion (e.g., one or more domains) thereof fused or bonded to heterologous polypeptide.

In some embodiments, the costimulatory molecule agonist is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

In some embodiments, administration of a combination of agents of the invention is combined with an effective dose of an agent that increases patient hematocrit, for example erythropoietin stimulating agents (ESA). Such agents are known and used in the art, including, for example, Aranesp® (darbepoetin alfa), Epogen® NF/Procrit® NF (epoetin alfa), Omontys® (peginesatide), Procrit®, etc.

Other combination therapies include administration with cell-specific antibodies, for example antibodies selective for tumor cell markers, radiation, surgery, and/or hormone deprivation (Kwon et al., Proc. Natl. Acad. Sci U.S.A., 96: 15074-9, 1999). A number of antibodies are currently in clinical use for the treatment of cancer, and others are in varying stages of clinical development. Antibodies of interest for the methods of the invention may act through ADCC, and are typically selective for tumor cells, although one of skill in the art will recognize that some clinically useful antibodies do act on non-tumor cells, e.g. CD20.

A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

The CD52 antigen is targeted by the monoclonal antibody alemtuzumab, which is indicated for treatment of chronic lymphocytic leukemia; colon cancer and lung cancer. CD22 is targeted by a number of antibodies, and has recently demonstrated efficacy combined with toxin in chemotherapy-resistant hairy cell leukemia.

Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

Monoclonal antibodies useful in the methods of the invention that have been used in solid tumors include, without limitation, edrecolomab and trastuzumab (herceptin). Edrecolomab targets the 17-1A antigen seen in colon and rectal cancer, and has been approved for use in Europe for these indications. Trastuzumab targets the HER-2/neu antigen. This antigen is seen on 25% to 35% of breast cancers. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')2, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies. The cross-linking of Fc receptors signals the effector cells to kill the target cells by cytolysis or apoptosis. In one embodiment, the induction is achieved via antibody-dependent cellular cytotoxicity (ADCC).

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest may be tested for their ability to induce ADCC (antibody-dependent cellular cytotoxicity). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

In addition to cancer therapies, the combination of agents of the invention are useful in other therapies in which monoclonal antibodies are administered for the purpose of depleting cells, e.g. in the treatment of inflammatory diseases by depletion of immune cells. For such purposes the combination of agents of the invention is administered in combination with a therapeutic antibody, e.g. with rituximab for depletion of B cells in inflammatory diseases and autoimmune conditions; alemtuzumab for multiple sclerosis; OKT3 for immunosuppression; others for bone marrow transplant conditioning; and the like.

"Concomitant administration" of a cancer therapeutic drug, ESA or tumor-directed antibody with a pharmaceutical composition of the present invention means administration with the high affinity CD47 reagent at such time that both the drug, ESA or antibody and the composition of the present invention will have a therapeutic effect. Such concomitant administration may involve concurrent (i.e. at the same time), prior, or subsequent administration of the drug, ESA or antibody with respect to the administration of a compound of the invention. A person of ordinary skill in the art would have no difficulty determining the appropriate timing, sequence and dosages of administration for particular drugs and compositions of the present invention.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Methods of Use

Methods are provided for treating, reducing or preventing cancer, including without limitation lymphomas, leukemias, carcinomas, melanomas, glioblastomas, sarcomas, myelomas, etc. as primary or metastatic cancers, by n a regimen comprising contacting the targeted cells with a combination of agents that modulate immunoregulatory signaling. Immunoregulatory modulating agents include (i) an agent that blockades CD47 activity; and (ii) an agent that agonizes an immune costimulatory molecule, e.g. CD137, thereby increasing in vivo phagocytosis of the tumor cells. The regimen may further comprise an agent that specifically binds to the target cell, e.g. an antibody or biologically active fragment or derivative thereof. Such methods include administering to a subject in need of treatment a therapeutically effective amount or an effective dose of the combined agents of the invention, including without limitation combinations of the reagent with a chemotherapeutic drug, a tumor-specific antibody, or an ESA.

Effective doses of the combined agents of the present invention, e.g. for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage of each agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including lymphomas, leukemias, carcinomas, melanomas, glioblastomas, sarcomas, myelomas, etc. For prophylactic applications, pharmaceutical compositions or medicaments are administered to a patient susceptible to, or otherwise at risk of disease in an amount sufficient to eliminate or reduce the risk, lessen the severity, or delay the onset of the disease, including biochemical, histologic and/or behavioral symptoms of the disease, its complications and intermediate pathological phenotypes presenting during development of the disease.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the compositions (e.g., agonist of costimulatory molecules; anti-CD47 agents, optionally antibodies that specifically bind to he targeted cells, and formulations thereof) of the invention and instructions for use. The kit can further contain a least one additional reagent, e.g. a chemotherapeutic drug, anti-tumor antibody, ESA, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose." Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXPERIMENTAL

Example 1

Combination of CD47 Blockade and CD137 Agonism in Targeting Cells for Immunodepletion As described in the co-pending international application claiming priority to U.S. provisional application 62/041,989, herein specifically incorporated by reference, depletion of hematopoietic cells expressing CD117 is significantly enhanced by administering a combination of an anti-CD47 agent, an agonist of CD137, and an antibody targeted to CD117; relative to a comparable treatment in which an anti-CD47 agent is administered with anti-CD117 in the absence of a CD137 agonist. These data demonstrate the principle of combining activities to deplete a targeted cell population, which principle is herein extended to targeting depletion of tumor cells.

Shown in FIG. 1, 8 week old DBA/2J mice were injected with p815 mouse mastocytoma cell line. 3 mice were injected with 250,000 untreated p815 cells incubated for two hours at 37 degree C., and administered via retro-orbital injections. 2 mice were injected with 250,000 p815 cells incubated with 100 ug/ml anti-c-Kit (ACK2) antibody+100 ug/ml Clone 3 (MIAP 410, anti-CD47 antibody) for two hours at 37 degree C., then injected RO. Mice were given IP injection of 500 ug anti-CD137 (Lob12.3) day 0, 2 and 4.

Mice were assessed for death, as P815 cells are not GFP+. One control untreated mouse died 4 weeks after the RO injection, another mouse died 12 weeks post injection. Both combination therapy treated test group mice were alive over 12 weeks post injection.

Example 2

In Vitro Synergy Experiment

An ADCC assay is performed using mouse or human NK cells (effectors) and mouse or human cancer cells (target cells). Mouse NK cells are isolated from peripheral blood, bone marrow, or spleens; human NK cells are isolated from peripheral blood. Human cancer cell lines or primary samples are labeled for use as target cells (e.g. with chromium or fluorescent dye).

The NK cells and cancer cells are combined in vitro, and co-culture with the following treatments:

Vehicle control (e.g. PBS)

CD137 agonist alone

CD47 antagonist alone

CD47 antagonist plus CD137 agonist

Tumor-binding antibody alone

Tumor-binding antibody+CD137 agonist alone

Tumor-binding antibody+CD47 antagonist alone

Tumor-binding antibody+CD47 antagonist plus CD137 agonist

ADCC is measured via chromium-release assay or flow cytometry cell death assays (e.q. Annexin V/DAPI staining). NK cell cytokine (e.g. IFN-gamma) release is measured via ELISA. The change in cell death and cytokine release in the presence of tumor-binding antibody+CD47 antagonist plus CD137 agonist is determined relative to the mono-therapies and dual therapies listed above.

Example 3

In Vivo Experiment Protocol

Cancer cells are injected into mice via subcutaneous, retroperitoneal, or peripheral blood injection and allowed to engraft. The animals are randomized into four treatment groups:
1. Vehicle control (e.g. PBS)
2. CD137 agonist alone
3. CD47 antagonist alone
4. CD47 antagonist plus CD137 agonist Mice are treated daily, three times per week, twice per week, or once per week with the respective treatments. Tumor burden is measured by tumor volume measurements, bioluminescence using labeled cancer cells (e.g. luciferase positive cells), and/or analysis of peripheral blood. CD137 expression on NK cells is measured in peripheral blood and in tumors. The overall survival of the mice is also measured.

Example 4

In Vivo Experiment Protocol for Synergy with Tumor-Specific Monoclonal Antibodies Cancer cells are injected into mice via subcutaneous, retroperitoneal, or peripheral blood injection and allowed to engraft. The animals are randomized into four treatment groups:
1. Tumor-binding antibody alone
2. Tumor-binding antibody+CD137 agonist alone
3. Tumor-binding antibody+CD47 antagonist alone
4. Tumor-binding antibody+CD47 antagonist plus CD137 agonist Mice are treated daily, three times per week, twice per week, or once per week with the respective treatments. Tumor burden is measured by tumor volume measurements, bioluminescence using labeled cancer cells (e.g. luciferase positive cells), and/or analysis of peripheral blood. CD137 expression on NK cells is measured in peripheral blood and in tumors. The overall survival of the mice is also measured.

Specific combinations of antibodies and tumors include without limitation the following:

Engraft mouse mastocytoma P815 cells into DBA/2 mice, treat with ACK2 (anti-mouse c-kit antibody) CD47/CD137 targeting therapies.

Engraft TUBO-EGFR cells into wild-type mice, treat with cetuximab (anti-human EGFR) and CD47/CD137 targeting therapies.

Engraft human melanoma SK-Mel-3 cells into RAG−/− mice, treat with SR-1 (anti-human c-kit) and CD47/CD137 targeting therapies.

Engraft B16 melanoma cells into wild-type mice, treat with TA99 (antibody targeting mouse B16 cells) and CD47/CD137 targeting therapies.

Engraft A20 mouse lymphoma cells into wild-type mice, treat with anti-mouse CD20 antibody and CD47/CD137 targeting therapies.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of targeting tumor cells for immunodepletion, the method comprising:
   contacting a population of cells comprising the targeted cells and a population of immune cells comprising NK cells and phagocytic cells with (i) an agent that blockades CD47 activity; (ii) an antibody that agonizes CD137; and (iii) an antibody that specifically binds to the targeted tumor cells specific for a marker selected from CD20, CD52, CD22, EGFR, CD117, and 17-1A antigen; in a dose effective to increase depletion of the targeted cells.

2. The method of claim 1, wherein the phagocytic cell population comprises macrophages.

3. The method of claim 1, wherein the contacting is performed on a mammal in vivo.

4. The method of claim 1, wherein depletion of the target cells is enhanced relative to the depletion observed with a monotherapy of (i) an agent that blockades CD47 activity; or (ii) an agent that agonizes CD137.

5. The method of claim 1 wherein the agent that blockades CD47 activity comprises a soluble SIRPα polypeptide.

6. The method of claim 5, wherein the soluble SIRPα polypeptide is a high affinity SIRPα variant.

7. The method of claim 6, wherein the soluble SIRPα polypeptide is CV1.

8. The method of claim 5, wherein the agent is a fusion protein comprising a SIRPα polypeptide.

9. The method of claim 8, wherein the agent is a monomer or a dimer.

10. The method of claim 1 wherein the agent that blockades CD47 activity is an anti-CD47 antibody.

11. The method of claim 1 wherein the agent that blockades CD47 activity is an anti-SIRPα antibody.

12. The method of claim 10, wherein the anti-CD47 antibody comprises an IgG4 Fc region.

13. The method of claim 10 wherein the antibody is 5F9-G4.

14. The method of claim 3, wherein said mammal is a mouse.

15. The method of claim 3, wherein said mammal is a human.

* * * * *